United States Patent [19]

Bates

[11] Patent Number: 4,854,159

[45] Date of Patent: Aug. 8, 1989

[54] JOURNAL BEARING SIMULATOR

[75] Inventor: Terence W. Bates, Ince, England

[73] Assignee: Shell Oil Company, Houston, Tex.

[21] Appl. No.: 231,938

[22] Filed: Aug. 15, 1988

[30] Foreign Application Priority Data

Aug. 28, 1987 [GB] United Kingdom ................. 8720377

[51] Int. Cl.[4] .............................................. G01N 33/26

[52] U.S. Cl. .............................................. 73/64; 73/10

[58] Field of Search ................................ 73/64, 59, 10

[56] References Cited

U.S. PATENT DOCUMENTS

| | | | |
|---|---|---|---|
| 2,114,029 | 4/1938 | Perry | 73/64 X |
| 2,337,414 | 12/1943 | Rieber | 73/10 |
| 2,808,563 | 10/1957 | Hornbostel | 73/64 X |
| 3,714,815 | 2/1973 | Hartert | 73/59 X |
| 3,785,196 | 1/1974 | Smith | 73/64 |
| 4,000,656 | 1/1977 | Moioli | 73/64 X |
| 4,267,722 | 5/1981 | Hendry | 73/64 X |

FOREIGN PATENT DOCUMENTS 805100 2/1981 U.S.S.R. ................................ 73/10

OTHER PUBLICATIONS

Oliver, D. R., *Rheol. Acta,* 21, pp. 527–529 (1982).

*Primary Examiner*—Stewart J. Levy
*Assistant Examiner*—Joseph W. Roskos

[57] ABSTRACT

A method and apparatus for measuring the load bearing capacity of engine oils under determined temperatures and shear rates. An eccentrically rotating cylindrical shaft (rotor) is used in a cylindrical journal bearing (stator) so arranged that the stator can be displaced from the center of rotation by a known amount. Measurements are made of minimum gap between the rotor and stator and of the force required to maintain the eccentrically rotating loaded shaft at a position such that the oil in the gap between rotor and stator achieves a shear rate between $1\times10^5$ and $1\times10^7\ s^{-1}$, typically $1\times10^6\ s^{-1}$.

12 Claims, 1 Drawing Sheet

JOURNAL BEARING SIMULATOR

FIELD OF THE INVENTION

The invention relates to a method and apparatus for assessing a lubricant's load bearing capacity.

BACKGROUND OF THE INVENTION

In the automotive industry, knowledge of the rheological properties of lubricants or engine oils and in particular the evaluation of the load bearing capacity of engine oils under realistic conditions in journal bearings is important.

Currently the measurement of the load bearing capacity of a lubricant is carried out by determining the minimum oil film thickness in the journal bearings of either a fired engine or dynamically or statically loaded motored rig.

Such tests are necessary for establishing the identity of the rheological properties which determine a lubricant's load bearing capacity in an operating journal bearing of an engine and for ranking the performance of lubricants in journal bearings.

However, such tests are difficult and time consuming to operate and therefore are not suitable for routine use either for product development or classification purposes.

It is therefore an object of the invention to provide a simple and rapid laboratory test to assess load bearing capacity.

It is another object of the invention to provide an easy-to-operate, relatively cheap bench apparatus for simulating the big-end and main journal bearings of the automotive (gasoline and diesel) engine.

SUMMARY OF THE INVENTION

The invention therefore provides an apparatus for measuring the load bearing capacity of engine lubricants under temperatures and shear rates typical of those applicable to journal bearings of operating engines, comprising an arrangement of two cylinders consisting of an outer non-rotating vertical cylinder (stator) and an inner, vertical cylindrical rotor, which, in use, is rotating about a vertical axis which is off-centre from both its own centre axis and that of the centre of the stator, a means for measuring the horizontal force exerted by the lubricant on the stator, a means for controlling the temperature and a means for displacing the stator from the centre of rotation of the rotor and a means for measuring a minimum gap between the rotor and stator.

The invention also provides a method for measuring the load bearing capacity of engine lubricants under temperatures and shear rates typical of those applicable to journal bearings of operating engines comprising the steps of rotating an inner, vertical cylindrical rotor about a vertical axis which is off-centre from both its own centre axis and that of the centre of an outer non-rotating vertical cylinder (stator) and measuring the horizontal force exerted by the lubricant on the stator, and controlling the temperature and shear rate of the lubricant.

BRIEF DESCRIPTION OF THE DRAWINGS

The invention will now be described by way of example in more detail by reference to the accompanying drawings, in which.

DETAILED DESCRIPTION OF THE DRAWINGS

Figure 1:
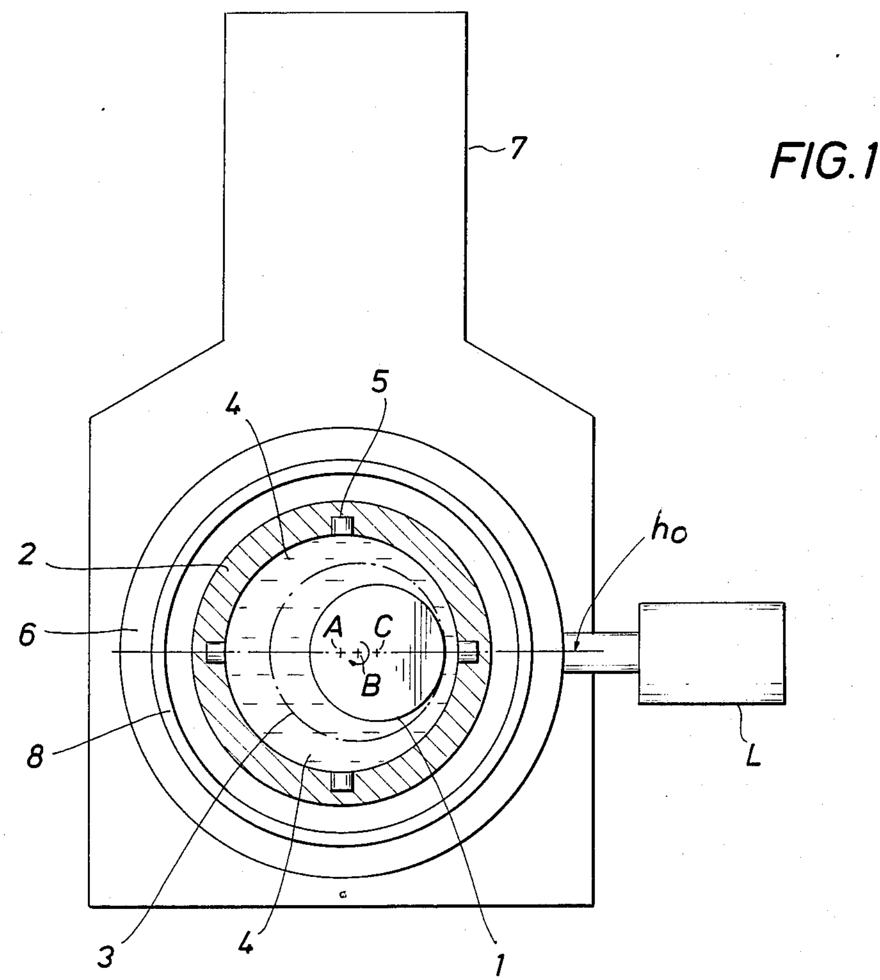
FIG. 1 represents schematically a top view of the rotor/stator part of the apparatus of the invention.
Figure 2:
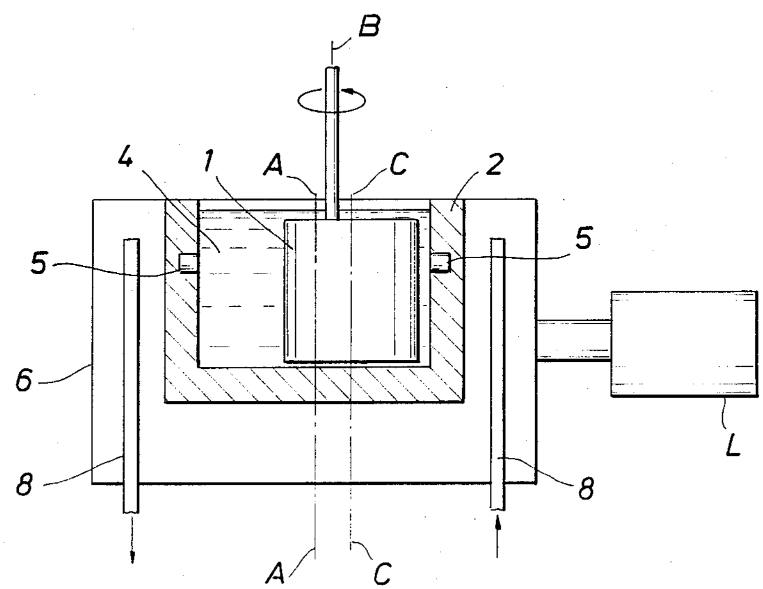
FIG. 2 represents a side sectional view of the apparatus of the invention.

Referring to FIGS. 1 and 2 the apparatus of the invention comprises an arrangement of two cylinders, consisting of an inner cylinder (rotor) 1 and an outer cylinder (stator) 2. The stator was filled with lubricant or engine oil 4. The rotor 1 has a centre axis C and, in use, rotates about an eccentric axis B which is also offset from the centre axis A of the stator. The graph $h_o$ represents a minimum oil film thickness. The dashed line 3 represents the locus of $h_o$.

The stator 2 is rigidly attached to a load cell L. The stator can be moved in any suitable manner relative to the rotor in any suitable increments (for example about 0.1 μm), thereby allowing the eccentricity ratio of the arrangement to be varied at will. The minimum gap between the rotor and stator is in the range of 0.1 to 10 μm, typically 0.5 to 2 μm. Shear rates of the minimum gap position are in the range of $1\times10^5$ to $1\times10^7$ $s^{-1}$, typically $1\times10^6$ $s^{-1}$.

The operation of the apparatus of the invention is as follows:

The rotor 1 is rotated continuously at high speed (i.e. up to 3000 r./min). In operation, the relative position of the rotation axis of the rotor and the centre axis of the stator are fixed and as a consequence of the high speed rotation of the rotor the oil exerts a force on the stator, this force being a measure of the load bearing capacity of the oil. Measurements are made of minimum gap between the rotor and stator and of the force required to maintain the eccentrically rotating loaded shaft at a position such that the oil in the gap between rotor and stator achieves a shear rate of $1\times10^5$ $s^{-1}$ to $1\times10^7$ $s^{-1}$, but typically is $1\times10^6$ $s^{-1}$, such shear rates being typical of those in main and big-end journal bearings of operating engines.

In effect, the operation is the opposite to that in, for example, the main and big-end bearing of an Internal Combustion engine where a load is imposed on the shaft (rotor) and the load bearing capacity of the lubricant determines the relative position of the shaft and bearing (stator).

The double eccentricity of the apparatus of the invention imparts "wobble" to the rotor thus leading to the type of dynamic motion characteristic of that present in journal bearings. In this way the dynamic loading present in big-end and main journal bearings of automotive engines is simulated. Such dynamic loading is essential for a proper simulation of big-end and main journal bearings.

The relative positions of the rotation axis of the rotor and the centre axis of the stator can be adjusted by any means suitable for the purpose 7 thus providing a means of adjusting the gap between the inner and outer cylinder to very fine tolerances (i.e. of the order of 0.1 micrometer).

Advantageously a combination of cam and lever principles can be applied in order to achieve such an adjustment.

It will be appreciated that the gap between rotor and stator can be measured in any way suitable for the purpose. Advantageously capacitance, inductance or resistance techniques can be used. For example up to four capacitance (or inductance or resistance) probes 5 can be mounted flush with the surface of the stator (but electrically insulated from it) and the oil film thickness measured by the technique described by T. W. Bates and P. Evans in *Proc. Jap. Soc. Lub. Engineers,* International Tribology Conference, Tokyo, Japan, July 8–10 (1985) p. 445.

Alternative techniques could be applied by those skilled in the art.

The oil is subjected to temperatures and shear rates typical of those applicable to journal bearings in automotive engines - namely temperatures of 100° to 150° C. and shear rates of $10^5$ to $10^7 s^{-1}$; the high shear rate can be achieved by the use of small (e.g. 0.1 to 5 μm) gaps and high rotational speeds between the eccentrically rotating rotor and stator.

Preferably, the temperature is controlled electrically or by circulating a thermostatically controlled fluid 8 through a jacketed outer stator 6.

It will be appreciated that the apparatus of the invention can be operated in a variety of ways; for example for ranking of load bearing capacity or measuring effects of oil rheology on load bearing capacity.

Various modifications of the present invention will become apparent to those skilled in the art from the foregoing description. Such modifications are intended to fall within the scope of the appended claims.

What is claimed is:

1. An apparatus for measuring the load bearing capacity of engine lubricants under temperatures and shear rates typical of those applicable to journal bearings of operating engines, comprising an arrangement of two cylinders consisting of an outer non-rotating vertical cylinder (stator) and an inner, vertical cylindrical rotor, which, in use, is rotating about a vertical axis which is off-centre from both its own centre axis and that of the centre of the stator, means for measuring the horizontal force exerted by the lubricant on the stator, a means for controlling the temperature, and a means for displacing the stator from the centre of rotation of the rotor, and a means for measuring a minimum gap between the rotor and stator.

2. The apparatus according to claim 1, wherein the rotor is rotated continuously at speeds up to 3000 r./min.

3. The apparatus according to claim 1, wherein the displacing means comprise a combination of cam and lever principles.

4. The apparatus according to claim 1, wherein the gap between rotor and stator is adjusted to tolerances of the order of 0.1 micrometer.

5. The apparatus according to claim 1, wherein the gap between stator and rotor is measured by capacitance, inductance or resistance techniques.

6. The apparatus according to claim 1, wherein the lubricant is subjected to temperatures of 100°–150° C.

7. The apparatus according to claim 1, wherein the lubricant is subjected to shear rates of $10^{5}$–$10^{7}$ $s^{-1}$.

8. A method for measuring the load bearing capacity of engine lubricants under temperatures and shear rates typical of those applicable to journal bearings of operating engines comprising the steps of rotating an inner, vertical cylindrical rotor about a vertical axis which is off-centre from both its own centre axis and that of the centre of an outer non-rotating vertical cylinder (stator) and measuring the horizontal force exerted by the lubricant on the stator, and controlling the temperature and shear rate of the lubricant.

9. The method according to claim 8 comprising the step of displacing the stator from the centre of rotation by a known amount.

10. the method according to claim 8, wherein the rotor is rotated continuously at speeds up to 3000 r./min.

11. The method according to claim 8, wherein the lubricant is subjected to temperatures of 100°–150° C.

12. The method according to claim 8, wherein the lubricant is subjected to shear rates of $10^{5}$–$10^{7}$ $s^{-1}$.

* * * * *